US009265479B2

(12) United States Patent
Yao et al.

(10) Patent No.: US 9,265,479 B2
(45) Date of Patent: Feb. 23, 2016

(54) ULTRASONIC DIAGNOSIS APPARATUS AND ULTRASONIC IMAGE PROCESSING APPARATUS

(75) Inventors: Cong Yao, Otawara (JP); Naohisa Kamiyama, Otawara (JP)

(73) Assignees: KABUSHIKI KAISHA TOSHIBA, Tokyo (JP); Toshiba Medical Systems Corporation, Otawara-shi (JP)

( * ) Notice: Subject to any disclaimer, the term of this patent is extended or adjusted under 35 U.S.C. 154(b) by 1280 days.

(21) Appl. No.: 12/986,414

(22) Filed: Jan. 7, 2011

(65) Prior Publication Data
US 2011/0172533 A1 Jul. 14, 2011

(30) Foreign Application Priority Data
Jan. 14, 2010 (JP) ................................. 2010-006111

(51) Int. Cl.
*A61B 8/08* (2006.01)
*A61B 8/13* (2006.01)
*G06T 7/00* (2006.01)

(52) U.S. Cl.
CPC ... *A61B 8/08* (2013.01); *A61B 8/13* (2013.01); *A61B 8/483* (2013.01); *A61B 8/5223* (2013.01); *G06T 7/0012* (2013.01); *G06T 7/0083* (2013.10); *G06T 2207/10132* (2013.01); *G06T 2207/30056* (2013.01)

(58) Field of Classification Search
None
See application file for complete search history.

(56) References Cited

FOREIGN PATENT DOCUMENTS

| JP | 7-8485 A | 1/1995 |
|---|---|---|
| JP | 2005-319080 A | 11/2005 |
| JP | 2007-512862 A | 5/2007 |
| JP | 4202966 | 10/2008 |
| JP | 2009-90102 A | 4/2009 |

OTHER PUBLICATIONS

"Intravascular Ultrasound Image Segmentation: AThree-Dimensional Fast-Marching Method Based on Gray Level Distributions" Marie-Hélène Roy Cardinal et al., IEE transactions, vol. 25, No. 5, May 2006.*
English language machine translation of JP 2005319080.*
Mariko Moriya, "Correlation between Parenchymal Echographic Pattern and Pathological Findings in Chronic Liver Disease B and C", Journal of Tokyo Women's Medical University, No. 3. vol. 63, Mar. 25, 2003, pp. 286-291.
Combined Office Action and Search Report issued Feb. 1, 2013 in Chinese Patent Application No. 201110008016.3 with English language translation.
Chen Fen, et al., "Multi-stage Water-ridge Line Algorithm Applied to 2D Medical Ultrasonic Imaging", Computer and Digital Engineering, vol. 35, Term 5, May 2007, pp. 132-137.
Office Action issued Oct. 15, 2013, in Japanese Patent Application No. 2010-006111 with English translation.

* cited by examiner

*Primary Examiner* — Amanda Lauritzen Moher
*Assistant Examiner* — Joseph M Santos Rodriguez
(74) *Attorney, Agent, or Firm* — Oblon, McClelland, Maier & Neustadt, L.L.P.

(57) ABSTRACT

According to one embodiment, a ultrasonic diagnosis apparatus comprises an ultrasonic scanning unit configured to scan a region including at least part of a liver of an object with an ultrasonic wave and acquire an echo signal associated with the liver, an image generating unit configured to generate an ultrasonic image of the liver based on an echo signal associated with the liver, and a calculation unit configured to calculate at least one of a first index indicating an irregularity degree of the liver and a second index indicating an irregularity feature of the liver by using the ultrasonic image of the liver.

16 Claims, 6 Drawing Sheets

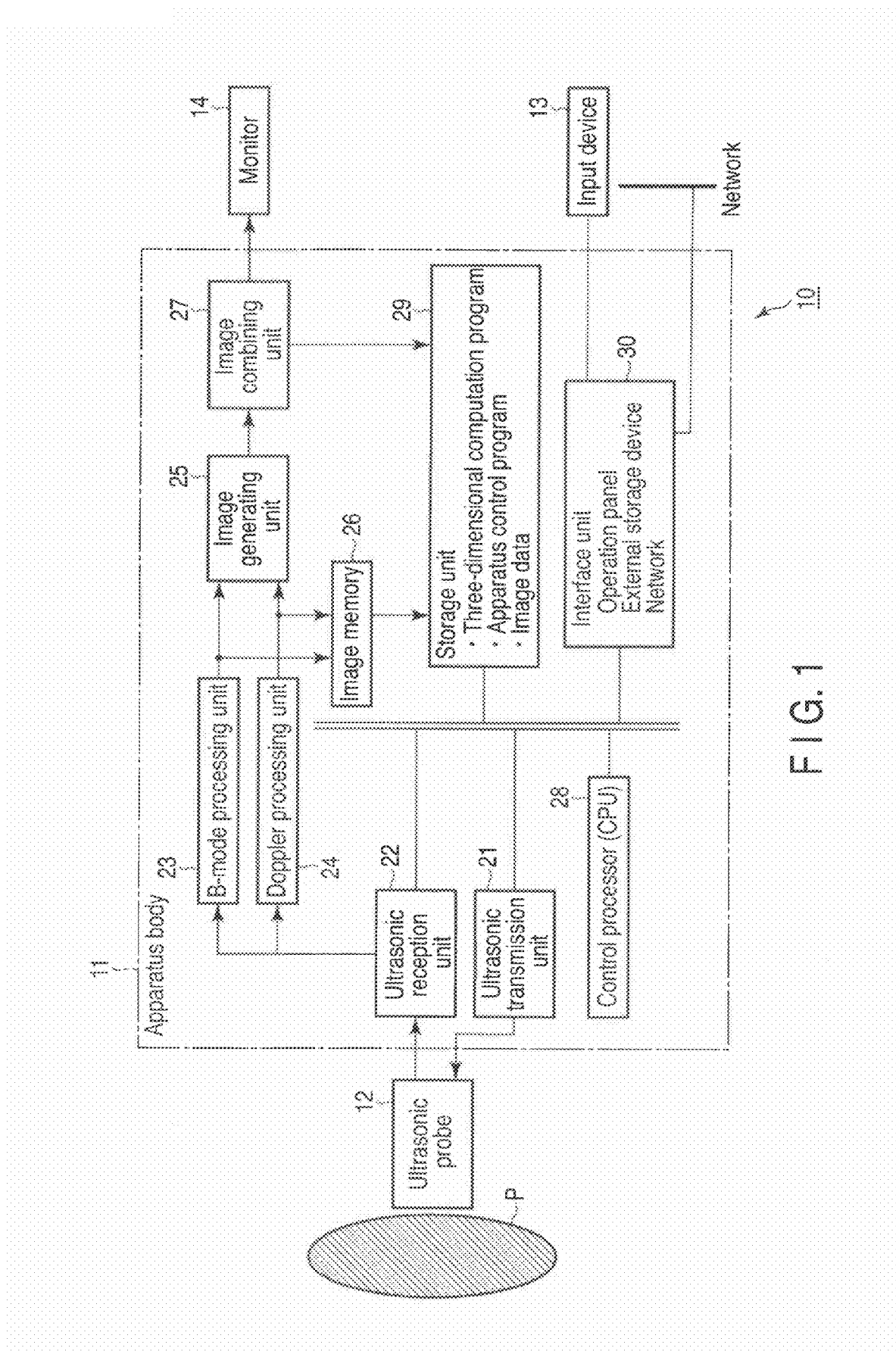
F I G. 1

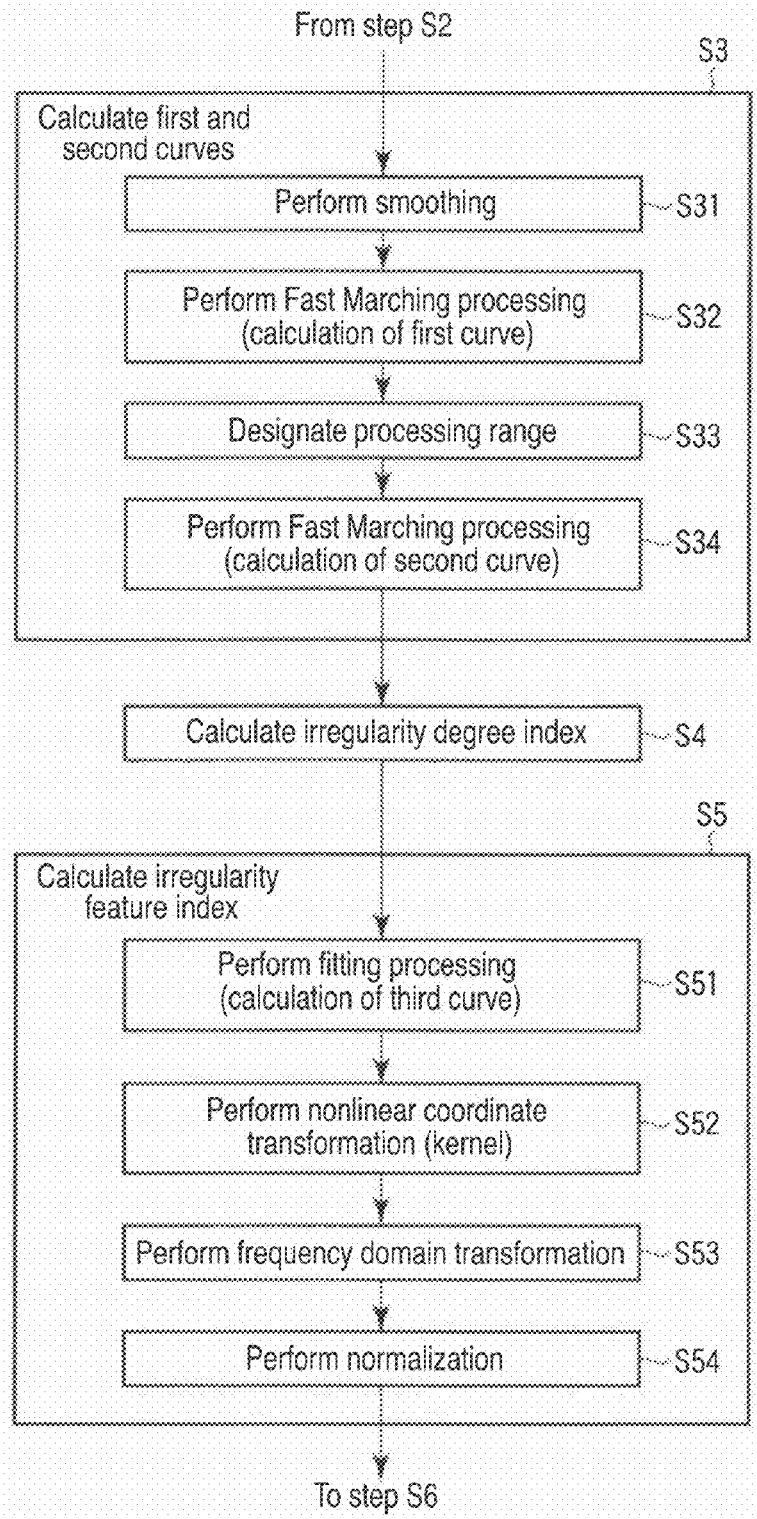
F I G. 3

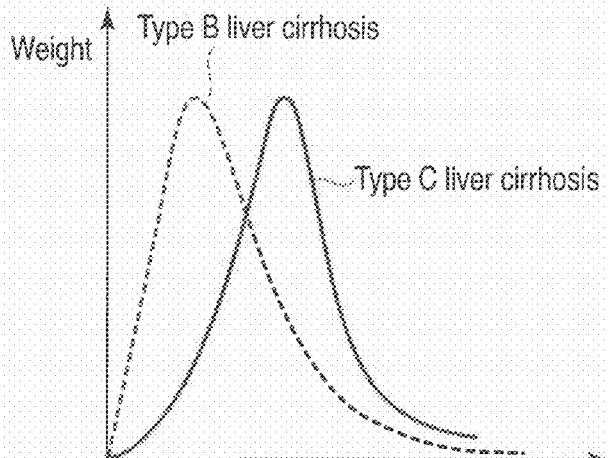
FIG. 8
| Liver function correspondence table ||||
|---|---|---|---|
| Irregularity degree | Irregularity feature |||
| | Type B liver c cirrhosis | Type C liver c cirrhosis | ... |
| ... | ... | ... | ... |
| ... | ... | ... | ... |
| 2mm | Stage 2 | Stage 3 | 0 |
| ... | ... | ... | ... |
| ... | ... | ... | ... |
FIG. 9
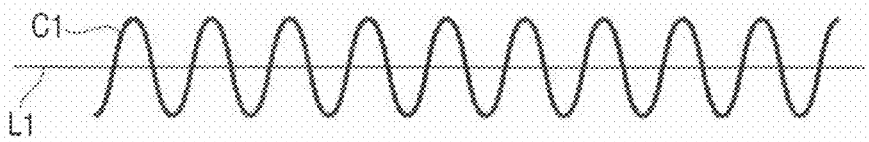
FIG. 10A
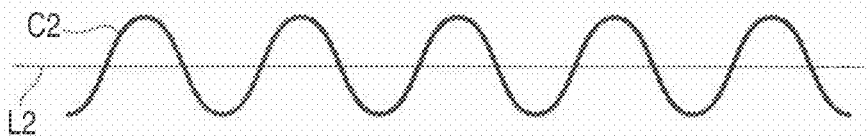
FIG. 10B

ULTRASONIC DIAGNOSIS APPARATUS AND ULTRASONIC IMAGE PROCESSING APPARATUS

CROSS-REFERENCE TO RELATED APPLICATIONS

This application is based upon and claims the benefit of priority from Japanese Patent Application No. 2010-006111, filed Jan. 14, 2010; the entire contents of which are incorporated herein by reference.

FIELD

Embodiments described herein relate generally to an ultrasonic diagnosis apparatus and ultrasonic image processing apparatus which can accurately evaluate the type and stage of liver disease using an ultrasonic image of the liver.

BACKGROUND

Ultrasonic diagnosis allows to display in real time how the heart beats or the fetus moves, by simply bringing an ultrasonic probe into contact with the body surface. This technique is highly safe, and hence allows repetitive examination. Furthermore, this system is smaller in size than other diagnosis apparatuses such as X-ray, CT, and MRI apparatuses and can be moved to the bedside to be easily and conveniently used for examination. In addition, ultrasonic diagnosis is free from the influences of exposure using X-rays and the like, and hence can be used in obstetric treatment, treatment at home, and the like.

Recently, there has been disclosed a technique for evaluating organs such as the liver by using such an ultrasonic diagnosis apparatus. This technique indicates the irregularity degree of the surface of the liver in the following manner: extracting a contour line by operation including smoothing and dividing the area of the portion sandwiched between the contour line and its approximate curve by the length of the approximate curve to obtain a normalized value based on the difference between the contour line and the approximate curve, thereby representing an irregularity. The technique colors the sandwiched portion and displays it on an image.

As a method of extracting the contour of an organ or the like by using an ultrasonic image or the like, for example, a method called the Fast Marching method is available. This method extracts an organ boundary from a tomogram by designating an initial contour inside the organ region and making ultrasonic waves continuously propagate from the initial contour in all directions. When making ultrasonic waves propagate, the method determines the path costs between pixels, that is, arrival time differences, according to local propagation velocities. Propagation velocities are obtained by a given expression such as the Eikonal equation dependent on the density values on an image. For example, the density values inside an organ are more uniform than those in a neighboring region of an organ boundary, and propagation velocities inside the organ are higher. That is, a contour propagates more quickly inside the organ. Separating a point at which the contour arrives from a point at which the contour does not arrive can quickly implement region segmentation.

As another method of extracting the contour of an organ or the like, the kernel method is available. According to this method, in data analysis, in order to grasp a nonlinear data structure, the original data is transformed into a form allowing easy analysis (a linear form in general) by applying nonlinear transformation to the original data.

The following problems, however, arise in the conventional method of evaluating organs in ultrasonic diagnosis.

That is, the conventional evaluation method executes smoothing in the process of extracting a contour line to remove noise near a boundary line. At this time, partial fine boundary irregularity information is lost together with noise. This partial fine boundary irregularity information includes a nodular pattern for determining the type of disease, and hence it may not be possible to make a satisfactory evaluation.

In addition, the conventional evaluation method evaluates a liver function as an irregularity based on the area of the portion sandwiched between a contour line and its approximate curve, that is, the variance relative to the approximate curve. However, the types and stages of liver disease vary, and there is not necessarily a one-to-one functional relationship between variances relative to approximate curves and liver functions. For this reason, simply using a variance relative to an approximate curve as an index for the diagnosis of a liver function may lead to an unsatisfactory result. More specifically, for example, as shown FIGS. 10A and 10B, with regard to contour lines C1 and C2 of two livers, approximate curves L1 and L2 are obtained, which extend across the respective curves. In this case, the variance of the contour line C1 relative to the approximate curve L1 is almost the same as that of the contour line C2 relative to the approximate curve L2. However, the comparison between the contour line C1 and the contour line C2 shows that their irregularity forms (for example, the degrees of zigzag) greatly differ from each other. Likewise, boundary lines of type C liver cirrhosis and type B liver cirrhosis in different stages may have the same variance.

BRIEF DESCRIPTION OF THE DRAWINGS

FIG. 1 is a block diagram of an ultrasonic diagnosis apparatus according to an embodiment;

FIG. 3 is a view for explaining the processing in steps S3, S4, and S5 of this liver diagnosis support processing in more detail;

FIG. 8 is a graph showing an example of the spectrum distribution normalized as an irregularity feature index;

FIG. 9 is a view showing an example of a liver function correspondence table associating irregularity degree indices and irregularity feature indices with liver functions; and FIGS. 10A and 10B are views for explaining a conventional liver function evaluation method.

DETAILED DESCRIPTION

Figure 2:
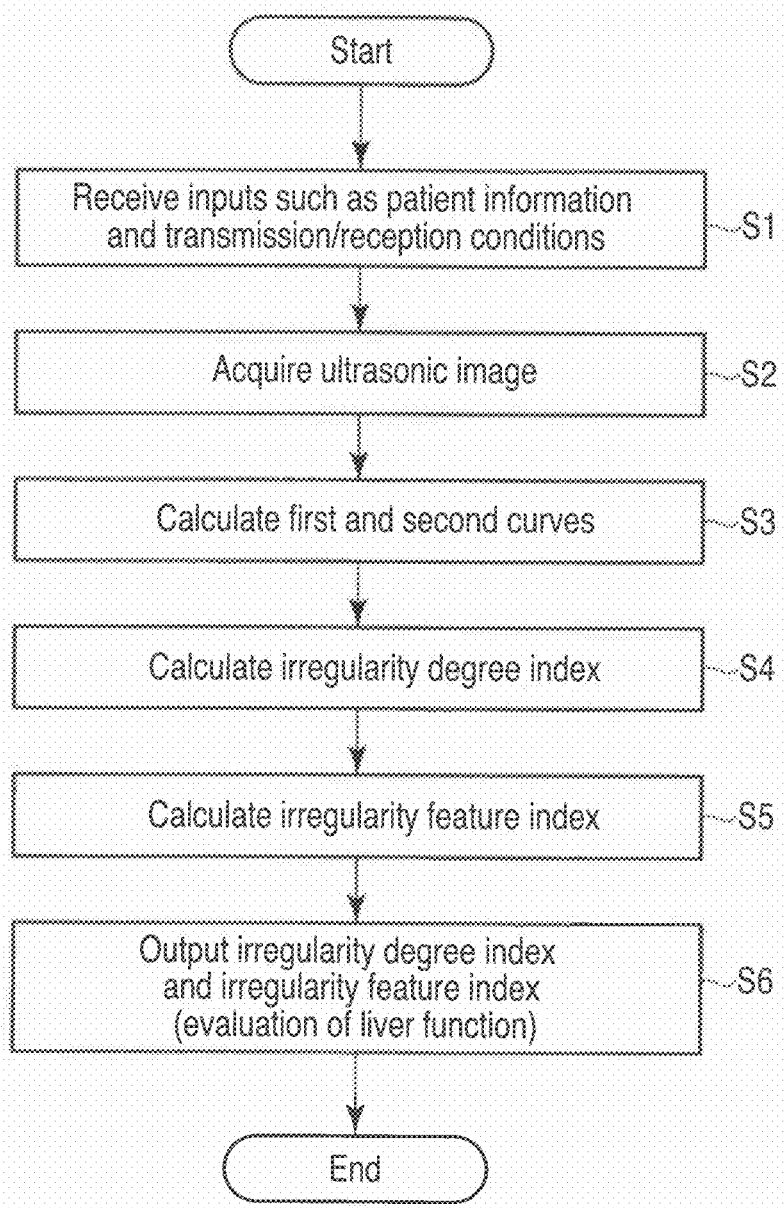
FIG. 2 is a flowchart showing a procedure for processing (liver diagnosis support processing) based on a liver diagnosis support function of this embodiment.

In general, according to one embodiment, an ultrasonic diagnosis apparatus comprises an ultrasonic scanning unit configured to scan a region including at least part of a liver of an object with an ultrasonic wave and acquire an echo signal associated with the liver, an image generating unit configured to generate an ultrasonic image of the liver based on an echo signal associated with the liver, and a calculation unit configured to calculate at least one of a first index indicating an irregularity degree of the liver and a second index indicating an irregularity feature of the liver by using the ultrasonic image of the liver.

The embodiments will be described below with reference to the views of the accompanying drawing. Note that the same reference numerals denote constituent elements having almost the same functions and arrangements, and a repetitive description will be made only when required. For the sake of a concrete description, each embodiment will exemplify the liver as a diagnosis target. However, the technical ideas of the present embodiments are not limited to this and is effective for predetermined organs other than the liver, such as the spleen and pancreas.

FIG. 1 is a block diagram of an ultrasonic diagnosis apparatus according to an embodiment. As shown in FIG. 1, an ultrasonic diagnosis apparatus 10 includes an ultrasonic probe 12, an input device 13, and a monitor 14, which are connected to the apparatus body. The ultrasonic diagnosis apparatus 10 also includes an ultrasonic transmission unit 21, an ultrasonic reception unit 22, a B-mode processing unit 23, a Doppler processing unit 24, an image generating unit 25, an image memory 26, an image combining unit 27, a control processor (CPU) 28, a storage unit 29, and an interface unit 30, which are incorporated in the apparatus body. The function of each constituent element will be described below.

The ultrasonic probe 12 includes a plurality of piezoelectric transducers which generate ultrasonic waves based on driving signals from the ultrasonic transmission unit 21 and convert reflected waves from an object into electrical signals, a matching layer provided for the piezoelectric transducers, and a backing member which prevents ultrasonic waves from propagating backward from the piezoelectric transducers. When ultrasonic waves are transmitted from the ultrasonic probe 12 to an object P, the transmitted ultrasonic waves are sequentially reflected by the discontinuity surface of acoustic impedance of an internal body tissue, and are received as an echo signal by the ultrasonic probe 12. The amplitude of this echo signal depends on an acoustic impedance difference on the discontinuity surface by which the echo signal is reflected. The echo produced when a transmitted ultrasonic pulse is reflected by the surface of a moving blood flow, cardiac wall, or the like is subjected to a frequency shift depending on the velocity component of the moving body in the ultrasonic transmission direction due to the Doppler effect.

The input device 13 includes various types of switches, buttons, a trackball, a mouse, and a keyboard which are connected to an apparatus body 11 and used to input, to the apparatus body 11, various types of instructions and conditions, an instruction to set a region of interest (ROI), various types of image quality condition setting instructions, and the like from an operator. When, for example, the operator operates the end button or FREEZE button of the input device 13, the transmission/reception of ultrasonic waves is terminated, and the ultrasonic diagnostic apparatus is set in a temporary stop state.

The monitor 14 displays morphological information in the living body and blood flow information as images based on video signals from the image combining unit 27.

The ultrasonic transmission unit 21 includes a trigger generating circuit, delay circuit, and pulser circuit (none of which are shown). The pulser circuit repeatedly generates rate pulses for forming transmission ultrasonic waves at a predetermined rate frequency fr Hz (period: 1/fr sec). The delay circuit gives each rate pulse the delay time required to focus an ultrasonic wave into a beam for each channel and determine a transmission directivity. The trigger generating circuit applies a driving pulse to the probe 12 at the timing based on this rate pulse.

The ultrasonic transmission unit 21 has a function of instantly changing a transmission frequency, transmission driving voltage, or the like to execute a predetermined scan sequence in accordance with an instruction from the control processor 28. In particular, the function of changing a transmission driving voltage is implemented by linear amplifier type transmission circuit capable of instantly switching its value or a mechanism of electrically switching a plurality of power supply units.

The ultrasonic reception unit 22 includes an amplifier circuit, A/D converter, and adder (none of which are shown). The amplifier circuit amplifies an echo signal received via the probe 12 for each channel. The A/D converter gives the amplified echo signals delay times necessary to determine reception directivities. The adder then performs addition processing for the signals. With this addition, a reflection component is enhanced from a direction corresponding to the reception directivity of the echo signal to form a composite beam for ultrasonic transmission/reception in accordance with reception directivity and transmission directivity.

The B-mode processing unit 23 receives an echo signal from the ultrasonic reception unit 22, and performs logarithmic amplification, envelope detection processing, and the like for the signal to generate data whose signal intensity is expressed by a luminance level. The image generating unit 25 causes the monitor 14 to display, as a B-mode image, a signal from the B-mode processing unit 23 whose reflected wave intensity is expressed by a luminance. At this time, this apparatus can provide image quality suiting user's taste by applying various image filters for edge enhancement, temporal smoothing, spatial smoothing, and the like to the signal.

The Doppler processing unit 24 frequency-analyzes velocity information from the echo signal received from the ultrasonic reception unit 21 to extract a blood flow, tissue, and contrast medium echo component by the Doppler effect, and obtains blood flow information such as an average velocity, variance, and power at multiple points. The obtained blood flow information is sent to the image generating unit 25, and is displayed in color as an average velocity image, a variance image, a power image, and a combined image of them on the monitor 14.

The image generating unit 25 generates an ultrasonic diagnosis image as a display image by converting the scanning line signal string for ultrasonic scanning into a scanning line signal string in a general video format typified by a TV format. The image generating unit 25 includes a dedicated processor and a memory to store image data. The image generating unit 25 reconstructs 3D volume data by coordinate transformation processing, interpolation processing, and the like using these components. The image generating unit 25 generates a tomogram obtained by scanning or an image using volume data (for example, an MPR image or volume rendering image) in response to an instruction from the input device 13. The liver diagnosis support function (to be described later) processes the region of interest set by the input device 13 by using the image generated by the image generating unit 25. This function outputs parameters representing an irregularity degree, irregularity feature, and liver function, which are calculated, to the monitor 14 via the image combining unit 27. Note that data before it is input to the image generating unit 25 is sometimes called "raw data".

The image memory 26 is a memory to store, for example, ultrasonic images corresponding to a plurality of frames immediately before a freeze. Continuously displaying (cinedisplaying) images stored in the image memory 26 can display an ultrasonic moving image.

The image combining unit 27 combines the image received from the image generating unit 25 with character information of various types of parameters, scale marks, and the like, and outputs the resultant signal as a video signal to the monitor 14. The image combining unit 27 generates a VR image with a scanned slice position which includes information indicating the position of the tomogram obtained by scanning in a volume rendering image. The image combining unit 27 also outputs parameters for supporting liver function diagnosis which are acquired by the liver diagnosis support function (to be described later) to the monitor 14 in a predetermined form under the control of the control processor 28.

The control processor 28 is a control unit which has a function as an information processing apparatus (computer) and controls the operation of the main body of this ultrasonic diagnosis apparatus. The control processor 28 reads out a control program for executing image generation/display and the like, a dedicated program for implementing the liver diagnosis support function (to be described later) from the storage unit 29, expands the programs in the memory of the processor, and executes computation/control and the like associated with various kinds of processing.

The storage unit 29 is used to archive transmission/reception conditions, control programs for executing image generation processing and display processing, diagnosis information (a patient ID, findings by a doctor, and the like), a diagnosis protocol, a body mark generating program, a dedicated program for implementing the liver diagnosis support function (to be described later), and other data groups. This storage unit is also used to, for example, archive images in the image memory 26, as needed. Data in the storage unit 29 can be transferred to an external peripheral apparatus via the interface unit 30.

The interface unit 30 is an interface associated with the input device 13, a network, and a new external storage device (not shown). The interface unit 30 can transfer data such as ultrasonic images, analysis results, and the like obtained by this apparatus to another apparatus via a network.

(Liver Diagnosis Support Function)

The liver diagnosis support function of the ultrasonic diagnosis apparatus 10 will be described next. In consideration of both the boundary line of the liver acquired by contour extraction processing including smoothing and the boundary line of the liver acquired by contour extraction processing including no smoothing, this function calculates at least one of an index indicating the irregularity degree of the boundary line of the liver (which will be simply referred to as an "irregularity degree index" hereinafter) and an index indicating a feature of the boundary line of the liver (which will simply referred to as an "irregularity feature index" hereinafter), and outputs the calculated indices in a predetermined form, thereby supporting liver diagnosis.

The following is the background to the consideration of both the boundary line of the liver acquired by contour extraction processing including smoothing and the boundary line of the liver acquired by contour extraction processing including no smoothing.

That is, the boundary surface of the normal liver is smooth without any irregularity. In contrast to this, the fibrosis of an abnormal organ such as the morbid liver has progressed due to various factors such as a virus, alcohol, and adiposity. This obscures the boundary of the liver and makes the boundary line of the liver have irregularity. This irregularity is also visualized on an ultrasonic image of the liver.

In addition, the form and degree of the irregularity of the boundary line of the liver correlate with the type of cause of a lesion and the stage of the lesion. The irregularity pattern of the boundary line of the liver varies depending on the type of lesion. When, for example, hepatic fibrosis progresses due to chronic hepatitis B, the liver parenchyma exhibits a relatively large nodular pattern. When hepatic fibrosis progresses due to chronic hepatitis C, the parenchyma exhibits a point-like pattern. It is possible to specify the type of lesion in the liver and the like by evaluating the occurrence of these irregularity patterns on the boundary of the liver, the degree of occurrence, and the like.

When evaluating the boundary line of the liver, the evaluation result depends on the extraction accuracy of the boundary line (contour) of the liver. As one of the contour extraction methods, the Fast Marching method is often used. In addition, since a propagation plane moves from the initial contour and stops at the true liver boundary, smoothing is required to remove a speckle pattern and the like. At the same time, however, smoothing will also delete the irregularity information of the boundary line.

For this reason, this liver diagnosis support function calculates an irregularity degree index and irregularity feature index for the evaluation of the liver function in consideration of both the boundary line of the liver acquired by contour extraction processing including smoothing and the boundary line of the liver acquired by contour extraction processing including no smoothing, and then outputs the calculated indices in a predetermined form.

FIG. 2 is a flowchart showing a procedure for processing (liver diagnosis support processing) based on this liver diagnosis support function. FIG. 3 is a flowchart for explaining the processing in steps S3, S4, and S5 of the liver diagnosis support processing in more detail. The contents of the processing in each step will be described below with reference to FIGS. 2 and 3.

[Reception of Inputs Such as Patient Information/Transmission Reception Conditions and Acquisition of Ultrasonic Image: Steps S1 and S2]

First of all, when the user inputs patient information and transmission/reception conditions (a depth of focus, transmission voltage, scanning range, and the like) via the input device 13, the control processor 28 stores various kinds of information and conditions in the storage unit 29 (step S1).

Figure 4:
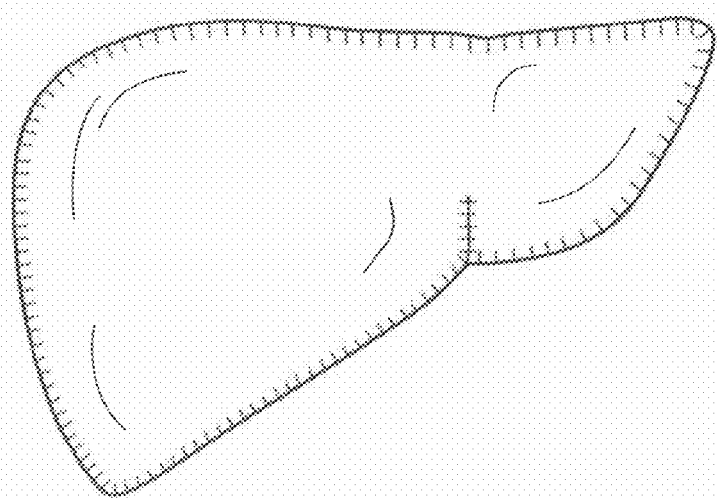
FIG. 4 is a schematic view of the liver.
Figure 5:
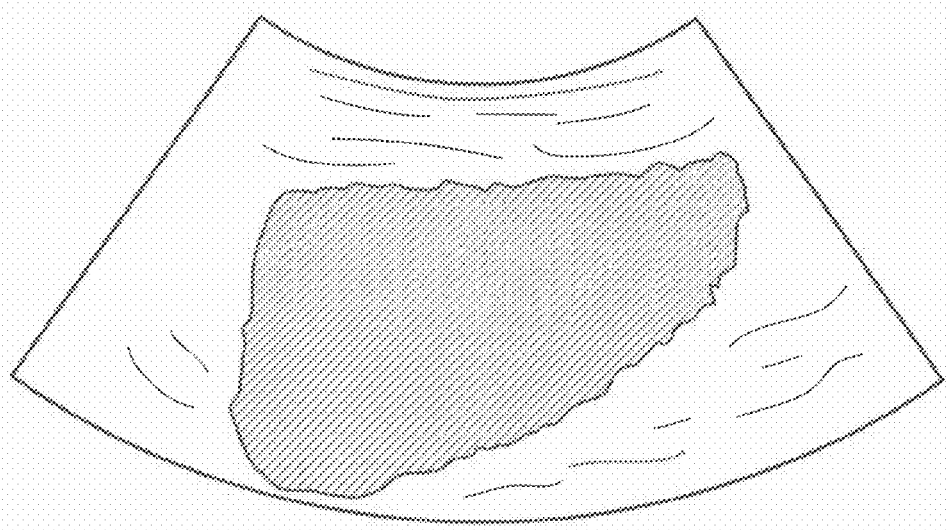
FIG. 5 is a view showing an example of an ultrasonic tomogram of the liver.

The control processor 28 then controls the ultrasonic probe 12, the ultrasonic reception unit 22, the B-mode processing unit 23, and the like in accordance with the input transmission/reception conditions to scan a region including at least part of the liver like that shown in FIG. 4 with ultrasonic waves, thereby acquiring an echo signal associated with the liver. The acquired echo signal is sent to the B-mode processing unit 23 via the ultrasonic reception unit 22. The B-mode processing unit 23 generates luminance data whose signal intensity is expressed by a luminance by performing logarithmic amplification, envelope detection processing, and the like for the received signal. The image generating unit 25 generates an ultrasonic image of the liver like that shown in FIG. 5 by using the luminance data received from the B-mode processing unit 23 (step S2).

[Calculation of First Curve/Second Curve: Step S3]

The control processor 28 then acquires the boundary line (first curve) of the liver acquired by contour extraction processing including smoothing and the boundary line (second curve) of the liver acquired by contour extraction processing including no smoothing (step S3).

The control processor 28 executes smoothing of an ultrasonic image including a real (substantial) liver boundary line

Figure 6A:
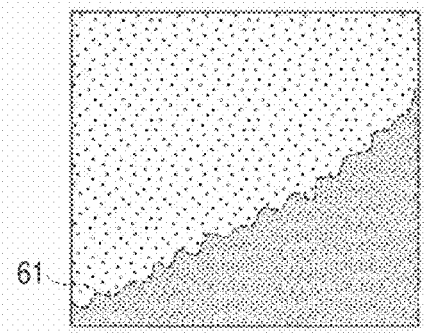
FIGS. 6A, 6B, 6C, and 6D are views for explaining the processing in step S3 in FIG. 2.
Figure 6B:
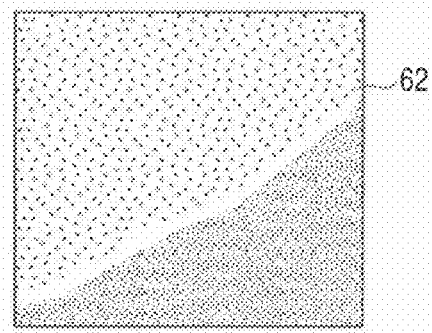

61 shown in FIG. 6A (step S31). This converts the ultrasonic image including the boundary line 61 normally having irregularity into an image including a thick belt-like boundary region 62 due to the averaging effect of luminance as shown in FIG. 6A. Note that the larger the irregularity of the boundary line 61, the larger the width of the boundary region 62.

Figure 6C:
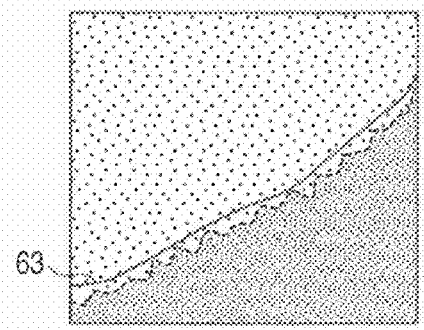
Figure 6D:
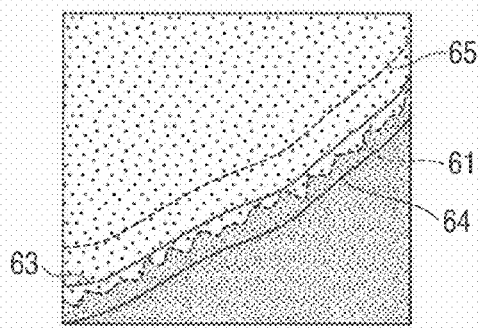

The control processor 28 calculates the first curve by executing the Fast Marching method for the smoothed ultrasonic image (step S32). A first curve 63 extracted by the Fast Marching method coincides with the inner side of the boundary region 62, as shown in FIG. 6C. Thereafter, the control processor 28 sets a region of interest (its boundary line) 64 and an initial contour 65 shown in FIG. 6D by using the calculated first curve. For example, the control processor 28 sets, as new regions of interest, all regions within the range of several pixels near the first curve, for example, with a distance of eight pixels from the first curve. The control processor 28 sets a new initial contour inside such a region of interest of the liver.

In addition, the control processor 28 acquires the second curve by executing Fast Marching processing for the ultrasonic image acquired in step S2 by using the region of interest and initial contour set in step S33 (step S34). Using the limited region of interest set in step S33 in this manner can minimize the influence of a speckle pattern and boundary leaks. The second curve acquired in step S34 has not undergone smoothing, and hence can hold the fine irregularity of the boundary line of the liver.

[Calculation of Irregularity Degree Index: Step S4]

The control processor 28 calculates the average value of the distances between the second curve and the first curve in the region of interest as an index indicating the irregularity degree of the boundary line of the liver (irregularity degree index) (step S4).

In the case of the normal liver, since the boundary line of the liver is normally smooth, the second curve almost overlaps the first curve. In the case of the abnormal liver affected by a disease, the second curve is detected outside the first curve. The distance between the first curve on the inside and the second curve on the outside depends on the irregularity degree of the boundary line of the liver. The irregularity degree reflects the degree of abnormality of the liver. The distance between the first and second curves is therefore a suitable index for evaluating the degree of abnormality of the liver.

[Calculation of Irregularity Feature Index: Step S5]

The control processor 28 calculates an irregularity feature index (step S3).

Figure 7A:
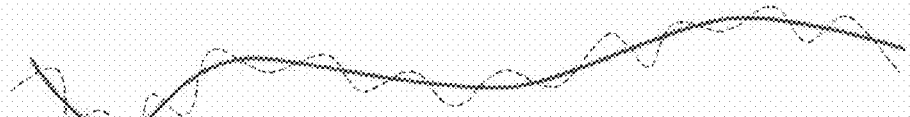
FIGS. 7A and 7B are views for explaining the nonlinear coordinate transformation processing executed in step S5.
Figure 7B:
Figure 7B:

That is, the control processor 28 calculates the third curve by executing fitting processing using the second curve indicating the boundary line of the liver (step S51). It is possible to execute this fitting processing by using nonlinear fitting that can reflect, for example, polynomial approximation, a quadratic curve, an exponential curve, and other contour forms. The control processor 28 then executes nonlinear coordinate transformation using the obtained third curve as a kernel function to acquire the coordinates of each point on the curve in the new space (step S52). This nonlinear coordinate transformation makes the contour points (dotted line) distributed around the third curve (fitting curve) shown in FIG. 7A be distributed around the straight line shown in FIG. 7B.

The control processor 28 then transforms the new space coordinates of the contour points into values in the frequency domain (step S53), and calculates an irregularity feature index by normalizing each obtained frequency component (step S54).

With the processing in this step, as an irregularity feature index, a normalized spectrum distribution like that shown in FIG. 8 is obtained. Note that it is possible to use, for example, Fourier transformation for the transformation to the frequency domain in step S53. However, this embodiment is not limited to this example, and it is possible to use other types of frequency domain transformation.

[Output of Irregularity Degree Index and Irregularity Feature Index: Step S6]

The control processor 28 then outputs the obtained irregularity degree index and irregularity feature index in a predetermined form (step S6).

For example, the monitor 14 displays the average of the distances between the second curve and the first curve and the spectrum distribution as an irregularity degree index and an irregularity feature index, as shown in FIG. 8, respectively, in a predetermined form. In the case of the abnormal liver, a spectrum distribution as an irregularity feature index correlates with the type of cause of a lesion and the stage of the lesion. In the case of type C liver cirrhosis, as shown in FIG. 8, the number of high-frequency components is larger than that in the case of type B liver cirrhosis. In the case of alcoholic cirrhosis, the number of high-frequency components becomes larger. Therefore, the doctor or the like can properly evaluate the liver function by observing the spectrum distribution as an irregularity feature index displayed on the monitor 14 using the previous knowledge about the hepatic properties.

It is also possible to display a liver function correspondence table like that shown in FIG. 9, which associates irregularity degree indices and irregularity feature indices with liver functions, as needed. Observing the displayed irregularity degree index/irregularity feature index/liver function correspondence table, the doctor or the like can determine the type of disease as type C liver cirrhosis from the spectrum distribution (irregularity feature index), and the stage of the disease as "3" from the fact that the irregularity degree index indicates an irregularity degree of about 2 mm, thus comprehensively evaluating the liver function.

Effects

According to the above arrangement, the following effects can be obtained.

This ultrasonic diagnosis apparatus sets a region of interest including the boundary line of the liver in an ultrasonic image of the liver, and calculates an irregularity degree index indicating the irregularity degree of the boundary line of the liver and an irregularity feature index indicating the feature of the boundary line of the liver in consideration of both the boundary line of the liver acquired by contour extraction processing including smoothing and the boundary line of the liver acquired by contour extraction processing including no smoothing. For example, the apparatus displays the calculated irregularity degree index and irregularity feature index in a predetermined form or displays them together with the liver function correspondence table in a predetermined form, as needed. Observing the displayed irregularity degree index and irregularity feature index, therefore, the doctor or the like can determine the type of liver disease, the stage (severity) of the disease, and the like, thus accurately and quickly making comprehensive evaluation. This can improve the accuracy of liver function diagnosis and contribute to a decrease in diagnosis time, thereby supporting liver function diagnosis.

Note that the present embodiment is not limited to the above embodiments, and constituent elements can be variously modified and embodied at the execution stage within the spirit and scope of each of the embodiments. The following is a specific modification.

For example, each function associated with each embodiment can also be implemented by installing programs for executing the corresponding processing in a computer such as a workstation and expanding them in a memory. In this case, the programs which can cause the computer to execute the corresponding techniques can be distributed by being stored in recording media such as magnetic disks (Floppy® disks, hard disks, and the like), optical disks (CD-ROMs, DVDs, and the like), and semiconductor memories.

In addition, the above technique can also use the images acquired by other medial image diagnosis apparatuses such as an X-ray computed tomography apparatus, magnetic resonance imaging apparatus, and X-ray imaging apparatus. Furthermore, incorporating the image processing function according to the embodiments allows each type of medical image diagnosis apparatus such as an X-ray computed tomography apparatus, magnetic resonance imaging apparatus, or X-ray imaging apparatus to use this technique.

Various embodiments can be formed by proper combinations of a plurality of constituent elements disclosed in the above embodiments. For example, several constituent elements may be omitted from all the constituent elements in each embodiment. In addition, constituent elements of the different embodiments may be combined as needed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnosis apparatus to evaluate the type and stage of liver disease comprising:
    a transmission and reception unit implemented by circuitry configured to transmit an ultrasonic wave to a region including at least part of a liver of an object and to receive an echo signal associated with the liver, via an ultrasonic probe;
    an image generating unit implemented by circuitry configured to generate an ultrasonic image of the liver in response to the echo signal associated with the liver; and
    a calculation unit implemented by circuitry configured to extract contour points and to calculate an approximate curve of the contour of the liver by using the ultrasonic image of the liver and to calculate a frequency distribution indicating an irregularity feature of the liver utilizing the positional relation between the approximate curve and the contour points of the liver, wherein the number of high-frequency components in the frequency distribution are utilize to determine the type and stage of the liver disease.

2. The apparatus according to claim 1, wherein the calculation unit acquires both a first boundary line of the liver acquired by contour extraction processing including smoothing and a second boundary line of the liver by contour extraction processing including no smoothing by using the ultrasonic image of the liver,
    calculate the approximate curve by using the first boundary line and the second boundary line, and
    calculates the frequency distribution by using the second boundary line.

3. The apparatus according to claim 2, wherein the calculation unit acquires the first boundary line and the second boundary line by using a Fast Marching method.

4. The apparatus according to claim 2, wherein the calculation unit calculates an average value of distances between the first boundary line and the second boundary line as the approximate curve.

5. The apparatus according to claim 4, wherein the calculation unit acquires the first boundary line and the second boundary line by using the Fast Marching method.

6. The apparatus according to claim 2, wherein the calculation unit calculates, as the frequency distribution, a spectrum distribution obtained by projecting the second boundary line on a kernel coordinate system of the approximate curve and transforming the second boundary line into a frequency domain.

7. The apparatus according to claim 6, wherein the calculation unit acquires the first boundary line and the second boundary line by using the Fast Marching method.

8. The apparatus according to claim 1, wherein the calculation unit further outputs a liver function correspondence table associating the approximate curve and the frequency distribution with a liver function.

9. An ultrasonic image processing apparatus to evaluate the type and stage of liver disease comprising:
    a transmission and reception unit implemented by circuitry configured to transmit an ultrasonic wave to a region including at least part of a liver of an object and to receive an echo signal associated with the liver, via an ultrasonic probe;
    an image generating unit implemented by circuitry configured to generate an ultrasonic image of the liver in response to the echo signal associated with the liver; and
    a calculation unit implemented by circuitry configured to extract contour points and to calculate an approximate curve of the contour of the liver by using the ultrasonic image of the liver and to calculate a frequency distribution indicating an irregularity feature of the liver utilizing the positional relations between the approximate curve and the contour points of the liver, wherein the number of high-frequency components in the frequency distribution are utilize to determine the type and stage of the liver disease.

10. The apparatus according to claim 9, wherein the calculation unit acquires both a first boundary line of the liver acquired by contour extraction processing including smoothing and a second boundary line of the liver by contour extraction processing including no smoothing by using the ultrasonic image of the liver,
    calculate the approximate curve by using the first boundary line and the second boundary line, and
    calculates the frequency distribution by using the second boundary line.

11. The apparatus according to claim 10, wherein the calculation unit acquires the first boundary line and the second boundary line by using a Fast Marching method.

12. The apparatus according to claim 10, wherein the calculation unit calculates an average value of distances between the first boundary line and the second boundary line as the approximate curve.

13. The apparatus according to claim 12, wherein the calculation unit acquires the first boundary line and the second boundary line by using the Fast Marching method.

14. The apparatus according to claim 10, wherein the calculation unit calculates, as the frequency distribution, a spectrum distribution obtained by projecting the second boundary line on a kernel coordinate system of the approximate curve and transforming the second boundary line into a frequency domain.

15. The apparatus according to claim 14, wherein the calculation unit acquires the first boundary line and the second boundary line by using the Fast Marching method.

16. The apparatus according to claim 9, wherein the calculation unit further outputs a liver function correspondence table associating the approximate curve and the frequency distribution with a liver function.

* * * * *